(12) United States Patent
Ahlmén

(10) Patent No.: US 11,771,860 B2
(45) Date of Patent: Oct. 3, 2023

(54) NASAL PATIENT INTERFACE ARRANGEMENT, BREATHING APPARATUS, AND METHOD FOR OPERATING A BREATHING APPARATUS

(71) Applicant: MAQUET CRITICAL CARE AB, Solna (SE)

(72) Inventor: Christer Ahlmén, Sollentuna (SE)

(73) Assignee: MAQUET CRITICAL CARE AB, Solna (SE)

( * ) Notice: Subject to any disclaimer, the term of this patent is extended or adjusted under 35 U.S.C. 154(b) by 728 days.

(21) Appl. No.: 16/611,757

(22) PCT Filed: Jun. 8, 2018

(86) PCT No.: PCT/SE2018/050597
§ 371 (c)(1),
(2) Date: Nov. 7, 2019

(87) PCT Pub. No.: WO2018/231128
PCT Pub. Date: Dec. 20, 2018

(65) Prior Publication Data
US 2020/0206448 A1     Jul. 2, 2020

(30) Foreign Application Priority Data
Jun. 13, 2017   (SE) .................................... 1750747-6

(51) Int. Cl.
*A61M 16/00*     (2006.01)
*A61M 16/06*     (2006.01)
(Continued)

(52) U.S. Cl.
CPC .... *A61M 16/0666* (2013.01); *A61M 16/0683* (2013.01); *A61M 16/0875* (2013.01); *A61M 16/201* (2014.02)

(58) Field of Classification Search
CPC .......... A61M 16/0666; A61M 16/0683; A61M 16/0875; A61M 16/201; A61M 16/0672; A61M 16/20
See application file for complete search history.

(56) References Cited

U.S. PATENT DOCUMENTS 6,994,089 B2    2/2006   Wood
8,333,200 B2    12/2012  Tero
(Continued)

FOREIGN PATENT DOCUMENTS

CN    101977648    2/2011
CN    102271740    12/2011
(Continued)

*Primary Examiner* — Samchuan C Yao
*Assistant Examiner* — Sarah B Lederer
(74) *Attorney, Agent, or Firm* — Fay Kaplun & Marcin, LLP

(57) ABSTRACT

A nasal patient interface arrangement is for transporting breathing gas from a pressurized gas supply to a patient. The arrangement provides a first bidirectional gas passage in contact with ambient air and receives nasally expired air. The arrangement includes an inspiratory air conduit connecting to a pneumatic unit. The arrangement also includes a nose adapter for bidirectional gas transport. The nose adapter is connected to a nose of the patient. The arrangement further includes a valve arrangement controlling the passage of gas through the first bidirectional gas passage. The arrangement provides a second bidirectional gas passage which is connected to the inspiratory air conduit, the nose adapter, and the first gas passage. The valve arrangement is substantially enclosed in the first bidirectional gas passage.

17 Claims, 5 Drawing Sheets

(51) Int. Cl.
*A61M 16/20* (2006.01)
*A61M 16/08* (2006.01)

(56) References Cited

U.S. PATENT DOCUMENTS

| | | | |
|---|---|---|---|
| 8,844,533 B2 * | 9/2014 | Allum | A61M 16/1045 |
| | | | 128/207.18 |
| 2002/0059935 A1 | 5/2002 | Wood | |
| 2002/0096178 A1 | 7/2002 | Ziaee | |
| 2007/0125377 A1 * | 6/2007 | Heinonen | A61M 16/203 |
| | | | 128/204.21 |
| 2011/0284001 A1 | 11/2011 | Tero | |
| 2011/0308520 A1 * | 12/2011 | McAuley | A61M 16/0683 |
| | | | 128/207.18 |
| 2012/0325218 A1 | 12/2012 | Brambilla et al. | |
| 2014/0066801 A1 * | 3/2014 | Tero | A61B 5/097 |
| | | | 128/205.24 |
| 2015/0000673 A1 | 1/2015 | Martin | |
| 2015/0040907 A1 | 2/2015 | Hakim et al. | |
| 2015/0083123 A1 * | 3/2015 | Tero | A61M 16/04 |
| | | | 128/205.25 |
| 2015/0128948 A1 * | 5/2015 | Rapoport | A61M 16/0866 |
| | | | 128/204.23 |

FOREIGN PATENT DOCUMENTS

| | | |
|---|---|---|
| CN | 106488784 | 3/2017 |
| DE | 3708146 | 9/1988 |
| JP | 2007229207 | 9/2007 |
| WO | 2005/014080 | 2/2005 |
| WO | 2010/076711 | 7/2010 |
| WO | 2012/149512 | 11/2012 |
| WO | 2013/132483 | 9/2013 |

* cited by examiner

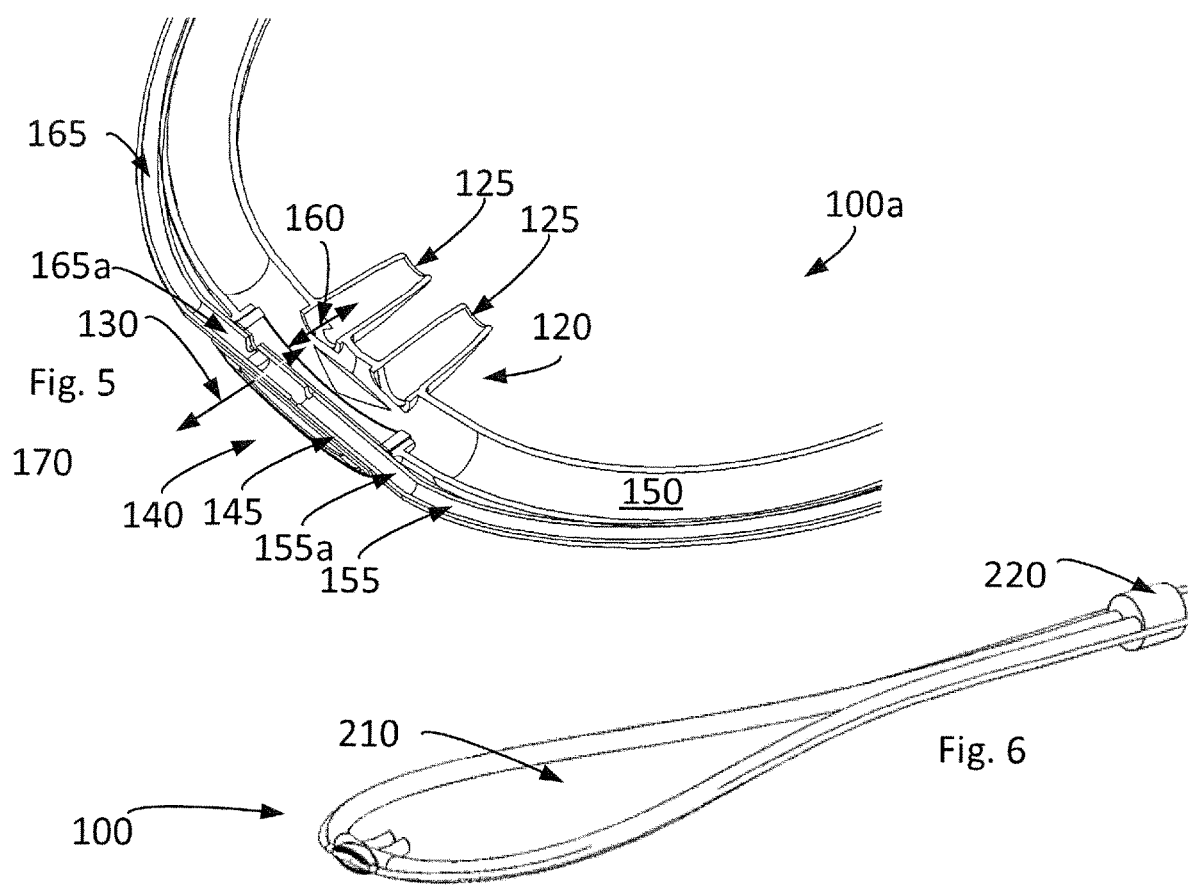
Fig. 5
Fig. 6
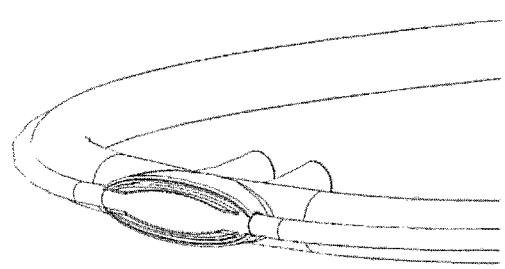
Fig. 7a
Fig. 7c
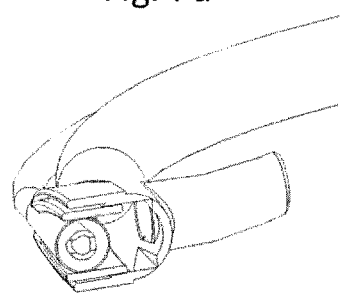
Fig. 7b
Fig. 7d

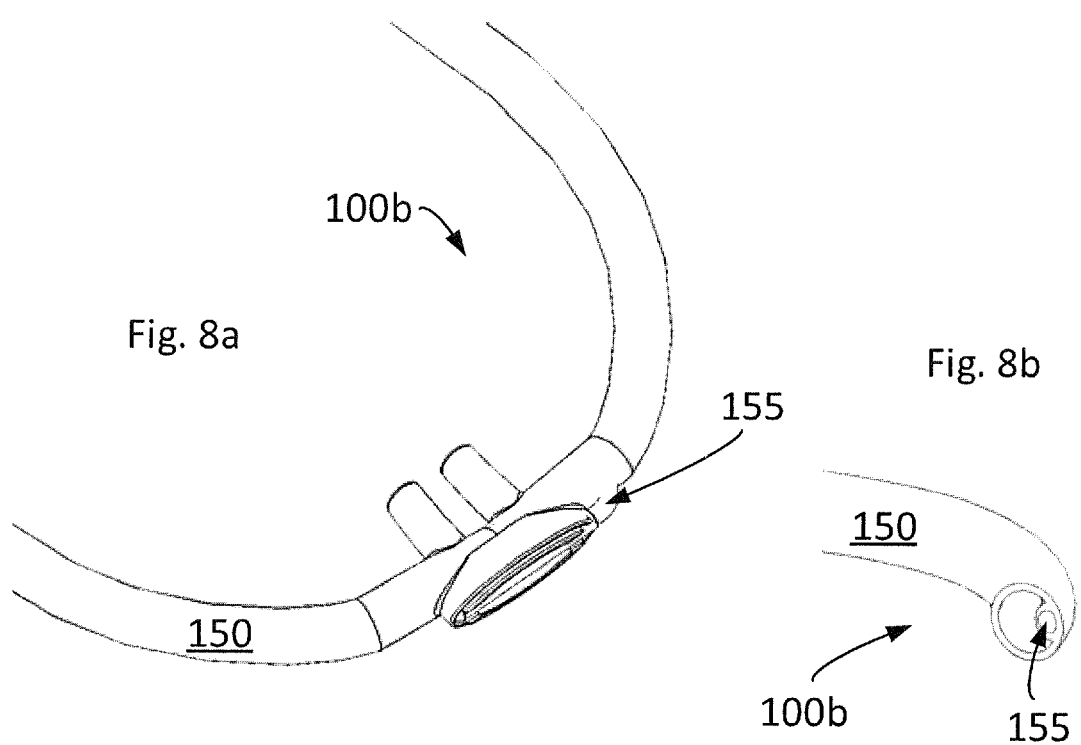
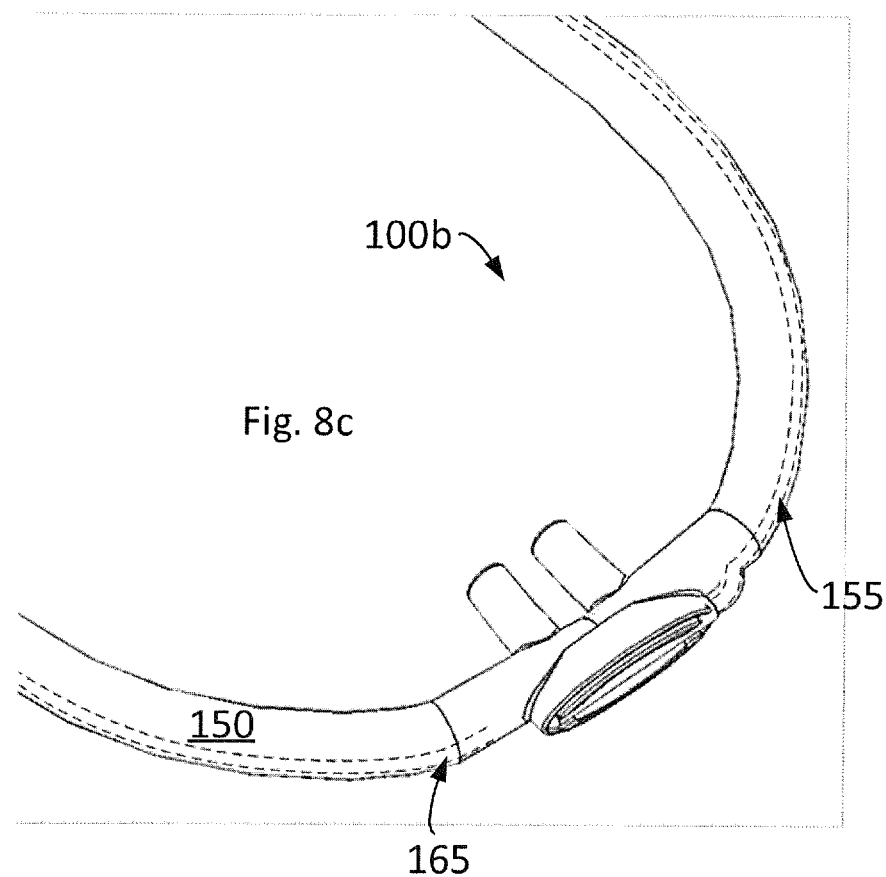

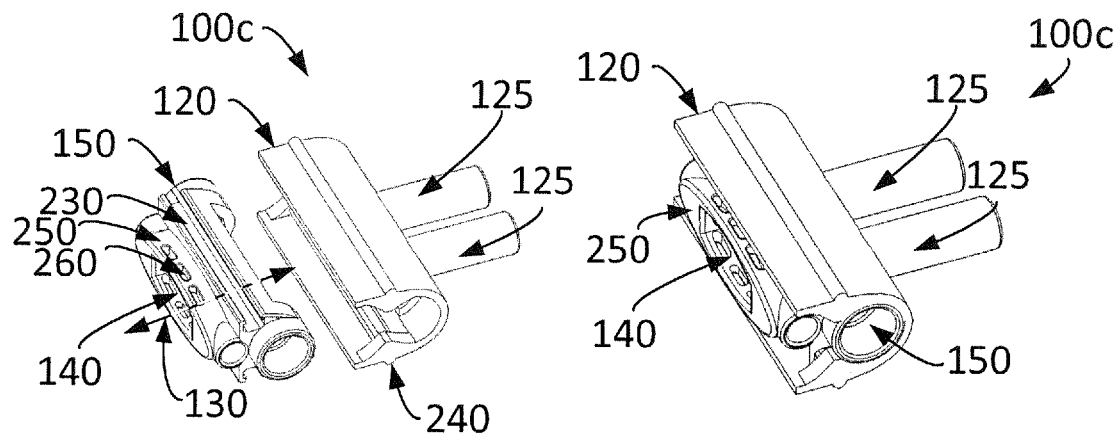
Fig. 9a    Fig. 9b
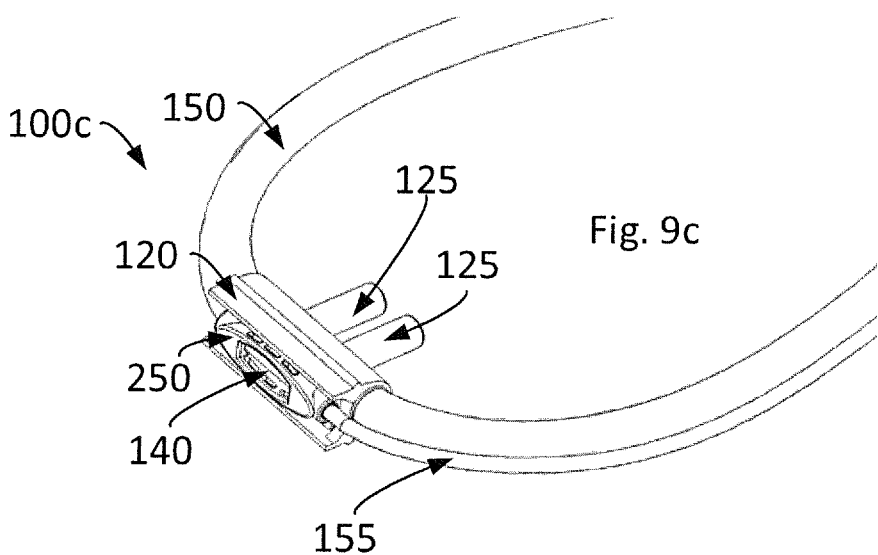
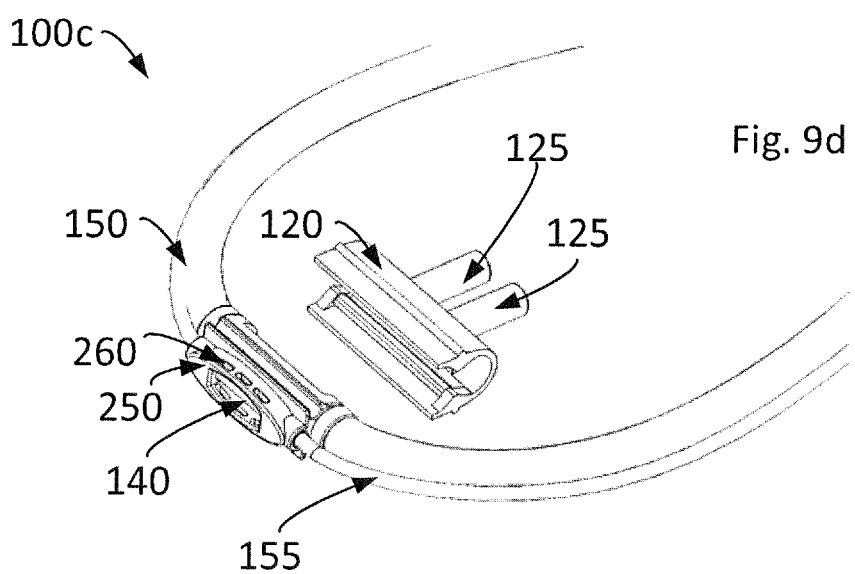

NASAL PATIENT INTERFACE ARRANGEMENT, BREATHING APPARATUS, AND METHOD FOR OPERATING A BREATHING APPARATUS

TECHNICAL FIELD

The present disclosure relates to a nasal patient interface arrangement, to a breathing apparatus, and to a method for operating a breathing apparatus.

BACKGROUND ART

Non-invasive ventilation is a commonly used form of treatment for patients in need of respiratory support. It is also preferred for neonatal patients. The main forms of treatments are nCPAP (nasal Continuous Positive Airway Pressure) and HFNC (High Flow Nasal Cannula). Even more advanced forms of treatment like the neurally synchronized mode NIV-NAVA (non-invasive ventilation neurally adjusted ventilatory assist).

The design and performance of the patient interface are very important factors for the result of the treatment. It should be easy to apply, remain in place, be well tolerated by the patient, and provide for a good ventilator performance. It should also have a small and neat design covering as little of the patients face as possible and not restrict the patient's movements.

It is also important that the manufacturing cost is low due to the fact that the patient interface normally is a disposable part.

Depending on the type of non-invasive nasal respiratory support, different types of nasal patient interfaces are used today. Some of the currently used interfaces, for example for nCPAP and for NIV-NAVA have in general a good performance regarding delivering pressure to the patient. They might, however, be cumbersome and difficult to apply to a patient. Other types of interfaces, for example for HFNC, usually comprise a cannula style interface and might have limited ventilator performance. This is due to the fact that the cannula does not deliver pressure well to the patient due to a high flow resistance in the cannula tubes.

One example of a patient interface is described in U.S. Pat. No. 8,844,533 B2. This patient interface uses a pillow cannula with a diaphragm valve.

US 2002/0096178 A1 describes a nasal mask interface with a balloon valve. The balloon valve is contiguous to an exhalation aperture and can close that aperture when inflated.

The valves in the interfaces of these two documents have a complex design.

SUMMARY OF THE INVENTION

The present disclosure relates to a nasal patient interface, breathing apparatus, and method for operating a breathing apparatus.

A nasal patient interface arrangement is for transporting breathing gas from a pressurised gas supply to a patient. The arrangement is adapted to provide a first bidirectional gas passage in contact with ambient air. The first bidirectional gas passage is adapted to receive nasally expired air. The arrangement comprises an inspiratory air conduit for connection to a pneumatic unit. The arrangement further comprises a nose adapter for bidirectional gas transport. The nose adapter is arranged to be connected to a patient's nose. The arrangement further comprises a valve arrangement for controlling the passage of gas through the first bidirectional gas passage. The arrangement is adapted to provide a second bidirectional gas passage which is connected to the inspiratory air conduct, to the nose adapter, and to the first gas passage. The valve arrangement is substantially enclosed in the first bidirectional gas passage.

This has the advantage that a compact nasal patient interface can be provided. It is especially possible to design such an interface in a way that the mouth is not covered by the interface, even for babies or premature born babies. This especially allows parents to better see the face of their babies, to establish a better communication with them, and to establish a closer relation to their babies. Further it allows breastfeeding the baby. It further provides different gas passages for inhalation and exhalation, reducing the risk of re-breathing exhaled gases. Further, the nasal patient interface arrangement allows for a direct and/or non-bended flow path. This enables to provide a low flow resistance through the valve arrangement. A low flow resistance reduces the breathing work to be provided by the patient. This is especially useful for premature patients or for patients with low breathing capabilities. Even further, the nasal patient interface allows an effective clearance of mucus and condensate water.

In one embodiment, the valve arrangement comprises a tubular shaped valve element. The valve element is arranged to seal the first bidirectional gas passage when inflated. This allows restricting the gas flow to only the second bidirectional gas passage.

In one embodiment, the tubular shaped valve element comprises a balloon valve for controlling the passage of gas in the first bidirectional gas passage. The balloon valve is arranged to be piloted between a deflated state in which the balloon valve allows an air passage from the nose adapter via the first bidirectional gas passage to the ambient air, and an inflated state in which the balloon valve prevents an air passage from the nose adapter via the first bidirectional gas passage to the ambient air. This allows providing a straight and direct exhalation channel to ambient air.

The tubular shaped valve element is preferably elongated. This allows to provide a larger opening area than a circular valve design and thus a lower flow resistance. This is especially useful for premature patients due to the limited space between nose and mouth.

In one embodiment, the arrangement comprises a gas delivery passage. The gas delivering passage is arranged to deliver gas to the inside of the balloon valve for allowing inflation of the balloon valve. This allows for a compact construction as the same gas supply can be used for inflation and for breathing. This also allows for a fail-safe arrangement as a stop in gas supply will prevent inflating of the balloon valve and thus allow a passage between nose adapter and ambient air so that breathing can be assured even if there would be a failure in a breathing apparatus, in a gas supply, or the like.

In one embodiment the arrangement comprises a pressure measuring tube in fluid connection with the second bidirectional gas passage. This allows for improved control of the pressure and flow of the gas actually delivered to the patient as the point of measurement is close to the patient.

In one embodiment the gas delivery passage and/or the pressure measuring tube are arranged to run alongside the inspiratory air conduit. This allows for a compact design.

In one example, the gas delivery passage and/or the pressure measuring tube are arranged inside the inspiratory air conduit. This reduces the number of visible components. This can be especially appealing for family members of a patient since the visible complexity of components which are connected to the patient are reduced. This can help in reducing the worrying of the family members.

In one embodiment, the nose adapter comprises at least one prong being arranged to be input to at least one nostril of the nose. This allows for an easy and space saving connection to the nose of a patient.

In one embodiment, the valve arrangement is arranged to be situated at a distance to the nose of the patient which is less than about 2 cm when the nose adapter is connected to the nose of the patient. This especially provides a compact design. In one example, the distance is less than 1 cm.

In one embodiment, the inspiratory air conduit comprises at least one tube being connected between the nose adapter and the breathing gas supply.

In one embodiment, the valve arrangement is arranged to be at least partly inflated during inhalation of the patient. This allows that mainly breathing gas is supplied to the patient during inhalation.

In one embodiment, the valve arrangement is arranged to be at least partly deflated during exhalation of the patient. This allows assuring a direct exhalation path to ambient air.

In one embodiment, the arrangement further comprises a bracket. The bracket is arranged to enclose the valve arrangement in a longitudinal extension. This allows for increased stability. This also allows assuring the functioning of the interface in case the patient lies head-down. In one embodiment, at least one hole is provided in the first gas passage. This also assures the functioning of the interface in case the patient lies head-down.

In one embodiment, the inspiratory air conduit and the nose adapter are constructed as one-piece. This reduces the complexity when operating the arrangement. It further reduces the number of possible seams where impurity can enter the arrangement when in operation.

In one embodiment, the nasal patient interface arrangement is a high flow nasal cannula arrangement, HFNC arrangement.

At least some of the objectives are also achieved by a breathing apparatus. The breathing apparatus comprises the arrangement according to the present disclosure.

At least some of the objectives are also achieved by a method for operating a breathing apparatus. The method comprises the step of inflating a valve which is substantially enclosed in a first bidirectional gas passage so that the first bidirectional gas passage is at least partly blocked. The method further comprises the step of providing breathing gas through a second bidirectional gas passage from a pressure gas supply to a nose adapter of a patient so that the patient can inhale the breathing gas. The breathing gas is provided at least during a substantial fraction of an inhalation period of the patient. The method further comprises the step of deflating the valve so that a gas passage through the first bidirectional gas passage is allowed and so that the majority of exhaled gas from the patient can pass through the first gas passage to ambient air during an exhalation period of the patient.

The breathing apparatus and the method provide the advantages described in relation to the nasal patient interface arrangement.

In the summary only some of the possible embodiments and their advantages have been presented. Further embodiments and advantages will be presented in the following detailed description. Further advantages will also appear for a person skilled in the art when reading the detailed description and/or when applying/implementing the present disclosure.

BRIEF DESCRIPTION OF THE DRAWINGS

FIG. 5 depicts schematically a horizontal cross-section of the first embodiment of the present disclosure;

FIG. 6 depicts schematically a larger image of an embodiment of a nasal patient interface arrangement according to the present disclosure;

FIGS. 7a and b depict schematically an embodiment of the present disclosure in which the valve arrangement is deflated;

FIGS. 7c and d depict schematically an embodiment of the present disclosure in which the valve arrangement is inflated;

FIG. 8a-c depict schematically a second embodiment of the present disclosure; and FIG. 9a-d depict schematically a third embodiment of the present disclosure;

In the figures same reference numerals refer to the same elements throughout the figures.

DETAILED DESCRIPTION

In the following the invention will be described with the help of several embodiments. The embodiments have been chosen to illustrate a selection of various aspects of the present disclosure. It should, however, be understood that it is possible to combine features between different embodiments to arrive at further embodiments which are within the scope of the present disclosure.

Figure 1:
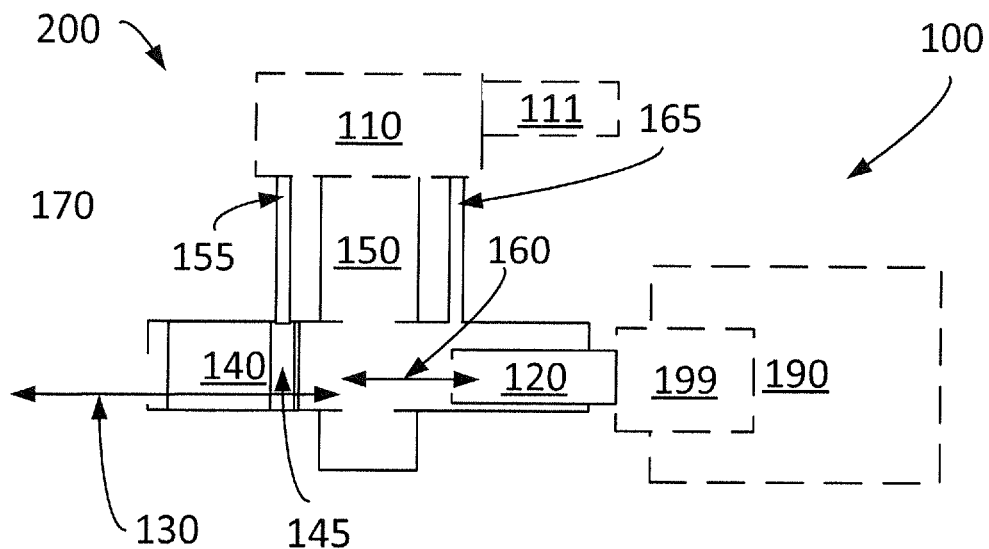
FIG. 1 depicts schematically a nasal patient interface arrangement according to an embodiment of the present disclosure.

FIG. 1 depicts schematically a nasal patient interface arrangement 100 and a breathing apparatus 200 according to an embodiment of the present disclosure. In the following, the nasal patient interface arrangement 100 might be simply denoted arrangement 100. The arrangement 100 is an arrangement for transporting breathing gas from a pressurised gas supply 111 to a patient 190.

The patient 190 can be any kind of patient, such as, for example, a grown up person, a teenager, a child, a baby, a neonatal baby, or a premature baby. Examples of breathing gases are air, oxygen, an oxygen-nitrogen mixture, a helium-oxygen mixture, so called "Heliox", or any other gas comprising one or several of the aforementioned components. The pressurised gas supply 111 can be part of a pneumatic unit 110 and/or a breathing apparatus 200, such as a ventilator or an anaesthesia machine.

The arrangement 100 is adapted to provide a first bidirectional gas passage 130. The first bidirectional gas passage is in contact with ambient air 170. The first bidirectional gas passage 130 can be enclosed by a bracket 180 and/or a bracket holder 185 as will be shown later. The first bidirectional gas passage 130 can be enclosed by an outer extension attachment 250 as will be shown later. The arrangement is adapted to receive nasally expired air, such as air from the nose 199 of the patient 190.

The arrangement 100 comprises an inspiratory air conduit 150 for connection to the pneumatic unit 110. The inspiratory air conduit 150 can comprise one or two tubes. The inspiratory air conduit can be arranged to deliver pressurized gas from the pressure gas supply 111 to the nose adapter 120. The pressure gas supply 111 can, for example, be a wall gas, a fan, a blower, a compressor, and/or a gas cylinder. In the shown example, the inspiratory air conduit 150 is only connected to the nose adapter 120 at one end. It should, however, be understood that the inspiratory air conduit 150 equally well can be connected to the nose adapter at both ends.

The arrangement 100 comprises further a nose adapter 120 for bidirectional gas transport. The nose adapter 120 is arranged to be connected to the nose 199 of the patient 190. The nose adapter 120 can comprise at least one prong (not shown in FIG. 1). The at least one prong is arranged to be input to at least one nostril of the nose 199. The nose adapter 120 can comprise only one prong. This might especially be useful in case the other nostril is needed for inserting a catheter, or any other tubes through the other nostril of the patient 190. In one example, the nose adapter comprises a nose mask (not shown). The nose mask can enclose the patients nostrils and nose.

The nose adapter 120 can comprise two prongs. This can especially be useful for providing an increased amount of breathing gas to the patient. The at least one prong can be adapted to cover the nostril(s) of the nose 120 fully or partly, for example around 80% of the nostril. The idea of the present disclosure provides for the possibility of reducing the risk of re-breathing exhaled gas as will become clear later. Therefore, it is possible to cover the nostril fully by a prong of the nose adapter 120 according to the present disclosure, since an emergency opening for avoiding total re-breathing is no longer needed.

The arrangement 100 comprises a valve arrangement 140 for controlling the passage of gas through the first bidirectional gas passage 130. The valve arrangement 140 can be arranged to be at least partly inflated during inhalation of the patient 190. The valve arrangement can be arranged to be fully inflated during inhalation of the patient 190. The valve arrangement can be arranged to block the passage, at least partly or fully, of gas through the bidirectional gas passage when the valve arrangement 140 is at least partly or fully inflated, respectively. The valve arrangement 140 can be arranged to be at least partly deflated during exhalation of the patient 190. Thereby a bidirectional flow of gas through the first bidirectional gas passage 130 will be allowed. This especially allows a flow of exhaled air from the patient through the first bidirectional gas passage 130 to ambient air. This especially avoids or at least reduces re-breathing of exhaled air by the patient 190.

The arrangement 100 is adapted to provide a second bidirectional gas passage 160. The second bidirectional gas passage 160 is connected to the inspiratory air conduct 150. The second bidirectional gas passage 160 can be at least partly inside the inspiratory air conduct 150. The second bidirectional gas passage 160 is connected to the nose adapter 120. The second bidirectional gas passage 160 is connected to the first gas passage 130. The second bidirectional gas passage 160 can be provided between the nose adapter 120, the first gas passage 130, and the tube(s) of the inspiratory air conduit 150. The second bidirectional gas passage 160 can be arranged to provide breathing gas to the nose 199 of a patient 190 when connected to the nose 190. The second bidirectional gas passage 160 can be connected to the pneumatic unit 110 and/or be part of the breathing apparatus 200. The second bidirectional gas passage 160 can be arranged to transport breathing gas.

The first and/or the second bidirectional gas passage 130, 160 can be arranged to be basically linear. The first and the second bidirectional gas passage 130, 160 can be arranged to be basically collinear to each other.

In one example, the valve arrangement 140 is arranged to be at least partly inflated during inhalation of the patient 190. This prevents at least partly an air flow from the ambient air 170 to the patient 190. This allows that the patient 190 will receive mainly breathing gas through the second bidirectional gas passage 160 during inhalation. In one example, the valve arrangement 140 is arranged to be fully inflated during inhalation of the patient 190. This can fully prevent an air flow from the ambient air 170 to the patient 190 during inhalation. When the valve arrangement 140 is fully closed, the second gas passage 160 will no longer be bidirectional. As an example, the second gas passage 160 can be arranged to unidirectionally transport breathing gas to the patient when the valve arrangement 140 is fully closed.

In a preferred embodiment the patient 190 will mainly receive breathing gas through the second bidirectional gas passage 160 during inhalation and will mainly exhale gas to the ambient air 170 through the first bidirectional gas passage 130.

The valve arrangement 140 is substantially enclosed in the first bidirectional gas passage 130. This allows for a compact design of the arrangement 100. This will become clear in connection to FIG. 2-9. In one example, the valve arrangement 140 is arranged to be situated at a distance to the nose 199 of the patient 190 which is less than about 2 cm when the nose adapter 120 is connected to the nose 199. This is especially useful for adults. In another example, the valve arrangement 140 is arranged to be situated at a distance to the nose 199 of the patient 190 which is less than about 1.5 cm when the nose adapter 120 is connected to the nose 199. In yet another example, the valve arrangement 140 is arranged to be situated at a distance to the nose 199 of the patient 190 which is less than about 1 cm when the nose adapter 120 is connected to the nose 199. This is especially useful for babies. The distance between the valve arrangement 140 and the nose 199 of the patient 190 might in general depend on the size of the patient 190. The valve arrangement 140 can comprises a tubular shaped valve element 145. The tubular shaped valve element 145 can be arranged to seal the first bidirectional gas passage 130 when inflated. In one example, the arrangement 100 comprises a bracket (not shown in FIG. 1). The bracket 180 can be arranged to enclose the valve arrangement 140 in a longitudinal extension. The bracket 180 can preferably be constructed out of a comparably rigid material, such as a hard plastic or metal. This can give a stable positioning of the valve arrangement 140 and prevent it from shifting in place. The bracket 180 can further assure that the valve arrangement still can be opened in case the patient lies with head down. In one example the first gas passage can be enclosed by an outer extension attachment 250 (not shown in FIG. 1). The outer extension attachment 250 can comprise at least one hole 260. The outer extension attachment 250 can comprise a central opening for the first gas passage 130.

The tubular shaped valve element 145 can for example be a balloon valve (not shown in FIG. 1). The balloon valve can be arranged for controlling the passage of gas in the first bidirectional gas passage 130. The balloon valve can be elongated. This can provide a better controllability and/or responsiveness of the valve. The balloon valve can be an inflatable hose. The balloon valve can be arranged to be piloted into a deflated state in which the balloon valve allows an air passage from the nose adapter 120 via the first bidirectional gas passage 130 to the ambient air 170. This is especially useful during exhalation. The balloon valve can be arranged to be piloted into an inflated state in which the balloon valve prevents an air passage from the nose adapter 120 via the first bidirectional gas passage 130 to the ambient air 170. This is especially useful during inhalation. Due to the preventing of the air passage the patient 190 will receive breathing gas through other means than the first gas passage 130, such as through the second gas passage 160. The tubular shaped valve element 145 is preferably placed orthogonal to the direction of flow as shown in the figures. However, it is also possible to have the valve element in axial direction to the flow inside a tube comprising the gas passage 130.

The arrangement 100 can comprise a gas delivery passage 155. The gas delivery passage 155 can be arranged to deliver gas to the inside of the balloon valve for allowing inflation of the balloon valve. The gas delivery passage 155 can be arranged to be connected to the pneumatic unit 110 and/or the breathing apparatus 200. The gas delivery passage 155 can be arranged to receive breathing gas. Thus the balloon valve can be inflated by breathing gas.

A failure to provide breathing gas to the patient 190 can in general put a patient at risk with an ordinary breathing apparatus. However, a breathing apparatus 200 according to the present disclosure will not inflate the balloon valve during inhalation in case no breathing gas can be supplied. Thus, the balloon valve will remain deflated in case no breathing gas can be supplied. As a result, the patient 190 will be able to receive ambient air 170 for inhalation through the first gas passage 130. Thus an automatic safety measure is provided in case there will be a problem with a breathing gas supply.

In one example, the arrangement 100 comprises a pressure measuring tube 165. The pressure measuring tube 165 can be in fluid connection with the second bidirectional gas passage 160. The pressure measuring tube 165 can be in fluid connection with the first bidirectional gas passage 130. This allows measuring of the pressure in the first and/or second gas passage 130, 160. In one example, the pressure measuring tube 165 connects to the first bidirectional gas passage 130 between the valve arrangement 140 and the nose adapter 120.

The gas delivery passage 155 and/or the pressure measuring tube 165 can be arranged to run alongside the inspiratory air conduit 150.

In the following, different embodiments of arrangements 100 will be described in relation to FIG. 2-9. FIG. 2-9 are schematically in that respect that some details might be omitted to focus on the ideas of the present disclosure. However, the elements depicted in FIG. 2-9 can in principle be provided as depicted and in the scale as depicted for arriving at workable products which embody the idea of the present disclosure. As long as nothing else is stated, elements of FIG. 2-9 will have the properties and functions as described in relation to FIG. 1.

Figure 2:
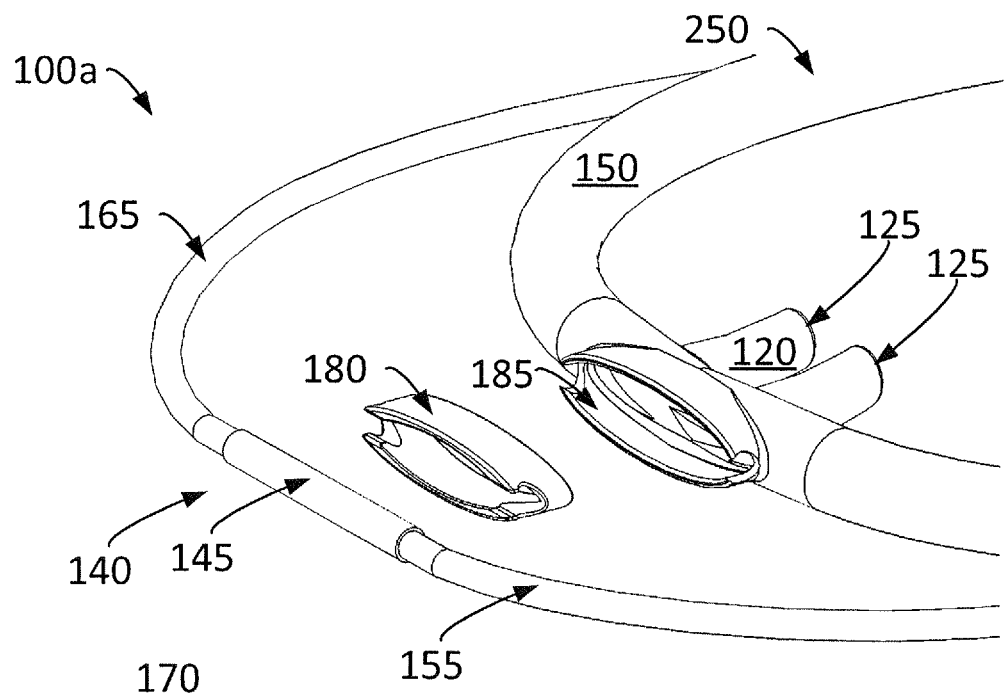
FIG. 2 depicts schematically an exploded view of a first embodiment of a nasal patient interface arrangement according to the present disclosure.
Figure 3:
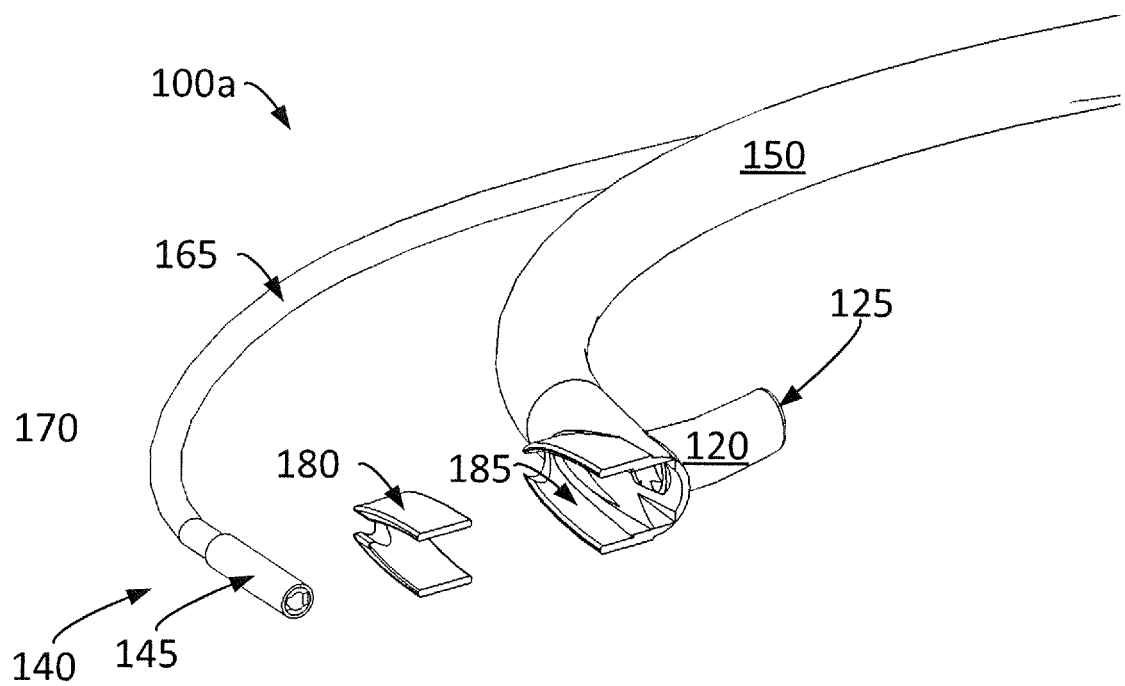
FIG. 3 depicts schematically an exploded view of a vertical cross-section of the first embodiment of the present disclosure.
Figure 4:
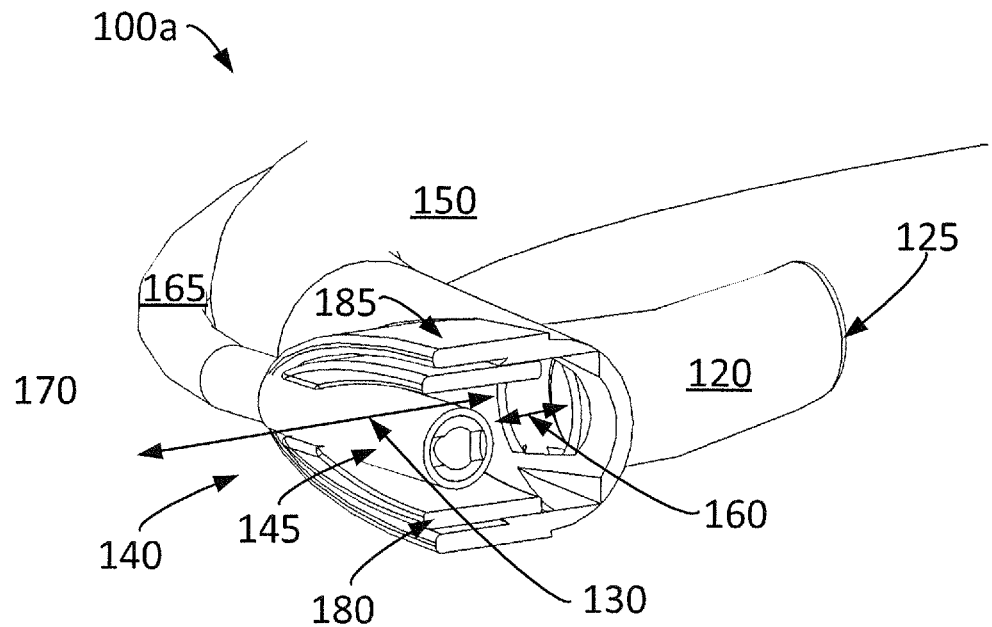
FIG. 4 depicts schematically a vertical cross-section of the first embodiment of the present disclosure.

A first embodiment 100a of the arrangement 100 is depicted in FIG. 2-5, wherein FIG. 2 depicts an exploded view, FIG. 3 depicts an exploded view of a vertical cross-section, FIG. 4 depicts a vertical cross-section, and FIG. 5 depicts a horizontal cross-section. The nose adapter 120 of the first embodiment 100a comprises two prongs. The valve arrangement 140 comprises the tubular shaped valve element 145. The tubular shaped valve element 145 is on a first side connected to the pressure measuring tube 165. The tubular shaped valve element 145 is on a second side connected to a gas delivery passage 155. The first side is opposite the second side. As can be seen, the outer design is basically symmetrically to a vertical axis. However, the inner design of the tubular shaped valve element 145 is not symmetrical to a vertical axis. A first conduit 155a inside the tubular shaped valve element 145 is connected to the gas delivery passage 155. The first conduit 155a extends through the largest part of the longitudinal extension of the tubular shaped valve element 145. The first conduit 155a has preferably no further opening than its connection to the gas delivery passage 155. Thus, when supplied by gas, the gas in the first conduit 155a can cause the tubular shaped valve element 145 to inflate. This will be discussed further in relation to FIG. 7. The first conduit 155a and the gas delivery passage 155 are preferably produced as one piece.

A second conduit 165a inside the tubular shaped valve element 145 is connected to the pressure measuring tube 165. The second conduit 165a extends through a smaller part of the longitudinal extension of the tubular shaped valve element 145. An opening is provided between the second conduit 165a and the first and second gas passage 130,160. Thus, it is possible to sense the pressure of the breathing gas and/or any other gas in the first and/or second gas passage 130, 160. A pressure measuring device can be connected to the side of the pressure measuring tube 165 which is not connected to the valve arrangement 140. The second conduit 165a is arranged in a longitudinal extension of the first conduit 155a. However, a stop element (not denoted by a reference number) can be arranged to prevent gas flow from the first conduit 155a to the second conduit 165a, or vice versa. The stop element is depicted (without reference number) in FIG. 5. The second conduit 165a and the pressure measuring tube 165 are preferably produced as one piece.

In the first embodiment 100a, the gas delivery passage 155 and the pressure measuring tube 165 are arranged to run alongside the inspiratory air conduit 150. The bracket 180 is arranged to enclose the valve arrangement 140 in the longitudinal extension. Thus the bracket constitutes a limit to which the tubular shaped valve element 145 can be inflated. At least when not inflated, the first bidirectional gas passage is provided from the nose through the prongs 125 of the nose adapter 120, through the bracket and alongside the deflated tubular shaped valve element 145 to the ambient air 170. The bracket can be of a strong and/or stiff material as discussed earlier in relation to the rigid material. The bracket can be arranged to be hold by a bracket holder 185. The bracket holder 185 can be arranged to enclose the bracket 180. The bracket holder 185 can be an opening of the nose adapter 120. The bracket holder 185 can be made out of soft plastic.

The second bidirectional gas passage 160 is provided from the inspiratory air conduit 150 through the nose adapter 120 to the prongs 125 and further to the nose of the patient when the prongs 125 are set inside the nostrils of the patient. When inhaling, the inflated tubular shaped valve element 145 preferably prevents, or at least substantially reduces, a gas passage through the first gas passage 130. Thus, breathing gas from the second gas passage 160 will be inhaled by the patient. When exhaling, the deflated tubular shaped valve element 145 will allow a gas passage through the first gas passage 130. Preferably the valve arrangement 140 is provided in a longitudinal extension of the prongs 125. The first gas passage provides a short and straight connection between the nostrils and the ambient air. Thus, the majority of the exhaled air will be released to the ambient air. Only a minor part of the exhaled air will stay in the nose adapter 120 and/or the inspiratory air conduit 150. Thus, re-breathing of exhaled gas will be prevented or at least significantly reduced.

It should be emphasised that the first embodiment 100a will also function without the bracket 180. As an example, an outer extension attachment 250 can be provided as will be discussed further in relation to the third embodiment. The outer extension attachment 250 can then be made of hard plastics.

FIG. 6 depicts a larger image of an embodiment of a nasal patient interface arrangement 100. The arrangement 100 can be an arrangement according to the first embodiment 100a or according to any other embodiment. The inspiratory air conduit can form a snare-like opening 210. The head of the patient can be placed in the opening. When the prongs are connected to the nose of the patient, an adjusting element 220, such as a slider, can be used to fix the arrangement 100 at the back of the head of the patient.

FIGS. 7a and b depict an embodiment of the present disclosure in which the valve arrangement is deflated and FIGS. 7c and d depict schematically an embodiment of the present disclosure in which the valve arrangement is inflated. FIGS. 7b and d are vertical cross-sections. Although the specific illustration relates to the first embodiment 100a, the same principle can apply to any other embodiment as well. In FIGS. 7a and b, the tubular shaped valve element is deflated. Consequently the first gas passage is open and exhaled gas from the nose of the patient can easily pass along the valve arrangement to the ambient air. In one example, the valve arrangement is arranged to not be completely deflated during exhalation. This has the advantage of keeping a certain pressure in the lungs of the patient. This might be helpful for preventing a collapse of the lungs. In FIGS. 7c and d, the tubular shaped valve element is inflated. Consequently, the first gas passage is fully closed, or at least closed to a larger extend. This prevents or at least greatly reduces a gas flow along the valve arrangement. As a result, gas which is inhaled by a patient while the valve arrangement is inflated will mainly be provided via the second gas passage.

FIG. 8a-c depict a second embodiment 100b of the present disclosure. The second embodiment 100b corresponds substantially to the first embodiment 100a. Not all components are denoted by reference signs again. However, the gas delivery passage 155 and the pressure measuring tube 165 are no longer on the outside of the inspiratory air conduit 150. Instead, the gas delivery passage 155 and/or the pressure measuring tube 165 are arranged inside the inspiratory air conduit 150. This is, for example, illustrated in FIG. 8b showing a vertical cross section of the inspiratory air conduit 150. Before connecting to the tubular shaped valve element 145, the gas delivery passage can extrude from the inspiratory air conduit 150 as can be seen in FIG. 8a. There is no need for the pressure measuring tube 165 to extend from the inspiratory air conduit 150 as the measuring tube 165 preferably has its opening on the side of the valve arrangement 140 which is oriented to the prongs. An example of how the gas delivery passage 155 and/or the pressure measuring tube 165 can be oriented inside the inspiratory air conduit 150 is illustrated by dashed lines in FIG. 8c. Thus, the inspiratory air conduit 150 can be provided as a multi-lumen tube, with two or more lumens.

Although depicted as several parts in the first and second embodiment 100a, 100b, it is equally well possible to construct the inspiratory air conduit 150 and the nose adapter 120 as one-piece.

FIG. 9a-d depict a third embodiment 100c of the present disclosure. The third embodiment 100c comprises a replaceable nose adapter 120. This might be useful for several reasons. First, the nose adapter might wear faster than other parts of the arrangement 100. Also, mucus, blood, and/or water might collect at the nose adapter 120. Thus, replacing the nose adapter alone and keeping the other parts of the arrangement 100c in place can save costs. Further, replacing the nose adapter alone saves time as this might be performed faster than disconnecting the whole arrangement 100 from the breathing apparatus 200.

Second, the distance between the nostrils differs from person to person. Instead of providing different sets of arrangements 100 for different distances between the nostrils, it is enough to only provide and/or store different sets of nose adapters which are adapted to different sizes of patients. This can save time, space, and cost. FIGS. 9a and d depict the arrangement 100c in a disassembled version. FIGS. 9b and c depict the arrangement 100c in an assembled version. In the shown embodiment, the nose adapter 120 encloses a part of the inspiratory air conduit 150 from above, below, and from the side which is oriented to the patient. It should be noted that FIGS. 9a and 9b only show a part of the inspiratory air conduit 150.

An extension 240 of the nose adapter 120 is arranged to engage with a recess 230 of the inspiratory air conduit 150. This can, for example, be on a side above and/or below the inspiratory air conduit 150. This can provide stability for the nose adapter 120 to not loosen from the inspiratory air conduit 150.

At least one hole 260 can be provided in the first bidirectional gas passage 130, such as an outer extension attachment 250. In the shown example, the first bidirectional gas passage 130 comprises six holes. Three holes are on a first side of the first bidirectional gas passage 130 and three holes are placed on a second side of first bidirectional gas passage 130. The second side is opposite the first side. The at least one hole 260 can provide a security opening in case the patient lies head-down. As can be seen from FIGS. 9b and 9c, the at least one hole 260 can provide an airflow through the first gas passage 130 even if the opening in the direct extension of the prongs would be covered. Even a bracket 180 and/or a bracket holder 185, such as shown, for example, in relation to the first and the second embodiment, can provide at least one hole 260. The at least one hole 260 in the bracket 180 and/or the bracket holder can provide a security opening as described above.

In one example of the third embodiment the nose adapter 125 and the prongs 120 are made out of soft plastic. In one example of the third embodiment the element comprising a part of the inspiratory air conduit 150 and the outer extension attachment 250 is made out of hard plastic. This element corresponds to the left element in FIG. 9a.

The inspiratory air conduit 150, the nose adapter 120, the valve arrangement, and any of the other described elements can be made out of plastics, such as silicon. The nasal patient interface arrangement 100 according to any of the shown embodiments can be a high flow nasal cannula arrangement, HFNC arrangement. In that case the valve arrangement 140 can be arranged to be closed as a standard configuration. The valve arrangement 140 can be arranged to open if the pressure exceeds a pre-determined pressure level. The pre-determined pressure level can relate to a pressure of the breathing gas delivered to the patient. The valve arrangement 140 can thus act as a security valve.

When terms as above or below have been used, this relates to how the elements are shown in the figures. It should be noted that these orientations can be different as the head of the patient can move, for example from sitting to lay in bed, or the like. However, the used expression should be used as if the arrangement 100 would be applied to a person sitting with a head in ordinary position. The first, second, and third embodiment 100a, 100b, and 100c have been depicted with prongs. It is, however, possible to use any other kind of nose adapter 120 in connection with the idea of the present disclosure as well. Especially, the idea of the present disclosure can also be used in connection with, for example, NIV-NAVA, nCPAP, Nasal intermittent positive pressure ventilation, non-invasive positive pressure ventilation, and oxygen therapy.

The present disclosure also relates to a method for operating a breathing apparatus. The breathing apparatus can comprise any element described in connection to FIG. 1-9. The method comprises the step of inflating a valve which is substantially enclosed in a first bidirectional gas passage. The inflating is performed in such a way that the first bidirectional gas passage is at least partly and preferably fully blocked.

The method further comprises the step of providing breathing gas through a second bidirectional gas passage from a pressure gas supply to a nose adapter of a patient so that the patient can inhale the breathing gas, wherein the breathing gas is provided at least during a substantial fraction of an inhalation period of the patient. The breathing apparatus might be adapted to determine the inhalation period of the patient. The inhalation period of the patient might be pre-determined.

The method further comprises deflating the valve so that a gas passage through the first bidirectional gas passage is allowed and so that the majority of exhaled gas from the patient can pass through the first gas passage to ambient air during an exhalation period of the patient. The breathing apparatus might be adapted to determine the exhalation period of the patient. The exhalation period of the patient might be pre-determined.

The method can comprise the step of measuring the pressure of the breathing gas in the first and/or second gas passage close to the nose adapter. The method can comprise the step of controlling the inflation and/or deflation of the valve based on a closed loop control. The closed loop control can be based on the measured pressure of the breathing gas.

The steps of the method can be repeated. The method can also comprise the step of purging the first and/or second gas passage from water and/or mucus by deflating the valve and increasing a flow of breathing gas while the valve is deflated. Thereby, the water and/or mucus can be transferred through the first gas passage to the ambient air. This can be performed periodically, intermittently, or on demand. Purging can be synchronized with the exhalation phase of the patient.

The method can contain the step of performing anything which has been described as functionality of any of the elements which have been described in relation to FIG. 1-9. Further, elements of the arrangement 100 and/or the breathing apparatus 200 can be arranged to perform any of the steps described in relation to the method for operating the breathing apparatus.

LIST OF ELEMENTS

100 Nasal patient interface arrangement
100a First embodiment of nasal patient interface arrangement
100b Second embodiment of nasal patient interface arrangement
100c Third embodiment of nasal patient interface arrangement
110 Pneumatic unit
111 Gas supply
120 Nose adapter
125 Prong
130 First bidirectional gas passage
140 Valve arrangement
145 Tubular shaped valve element
150 Inspiratory air conduct
155 Gas delivery passage
155a First conduit
160 Second bidirectional gas passage
165 Pressure measuring tube
165a Second conduit
170 Ambient air
180 Bracket
185 Bracket holder
190 Patient
199 Nose
200 Breathing apparatus
210 Opening
220 Adjusting element
230 Recess
240 Extension
250 Outer extension attachment
260 Hole

The invention claimed is:

1. A nasal patient interface arrangement for transporting breathing gas from a pressurised gas supply to a patient, the nasal patient interface arrangement being adapted to provide a first bidirectional gas passage in contact with ambient air and adapted to receive nasally expired air, the arrangement comprising:

an inspiratory air conduit connecting to a pneumatic unit;
a nose adapter configured for a bidirectional gas transport, wherein the nose adapter is arranged to be connected to a nose of the patient;
a valve arrangement controlling the passage of gas through the first bidirectional gas passage, the valve arrangement configured to be piloted between a deflated state, in which gas is passable through the first bidirectional gas passage, and an inflated state, in which the first bidirectional gas passage is at least partially blocked to prevent the passage of gas therethrough;
wherein the nasal patient interface arrangement is adapted to provide a second bidirectional gas passage which is connected to the inspiratory air conduct, the nose adapter, and the first gas passage, and
wherein the valve arrangement is substantially enclosed in the first bidirectional gas passage and is connected to the pneumatic unit via a gas delivery passage so that the gas delivery passage automatically receives breathing gas to pilot the valve arrangement from the deflated state toward the inflated state only when breathing gas is also being provided automatically through the inspiratory air conduit and the second bidirectional gas passage to the nose adapter.

2. The arrangement according to claim 1, wherein the valve arrangement includes a tubular shaped valve element and wherein the valve element is arranged to seal the first bidirectional gas passage when inflated.

3. The arrangement according to claim 2, wherein the tubular shaped valve element is a balloon valve controlling the passage of gas in the first bidirectional gas passage and wherein, in the deflated state, the balloon valve allows an air passage from the nose adapter via the first bidirectional gas passage to the ambient air, and in the inflated state, the balloon valve prevents an air passage from the nose adapter via the first bidirectional gas passage to the ambient air.

4. The arrangement according to claim 3, wherein the gas delivery passage is arranged to deliver gas to the inside of the balloon valve allowing the inflation of the balloon valve.

5. The arrangement according to claim 1, further comprising:
a pressure measuring tube in fluid connection with the second bidirectional gas passage.

6. The arrangement according to claim 5, wherein the gas delivery passage and/or the pressure measuring tube are arranged to run alongside the inspiratory air conduit.

7. The arrangement according to claim 5, wherein the gas delivery passage and/or the pressure measuring tube are arranged inside the inspiratory air conduit.

8. The arrangement according to claim 1, wherein the nose adapter includes at least one prong which is arranged to be input to at least one nostril of the nose.

9. The arrangement according to claim 1, wherein the valve arrangement is arranged to be situated at a distance to the nose which is less than 2 cm when the nose adapter is connected to the nose.

10. The arrangement according to claim 1, wherein the inspiratory air conduit includes at least one tube being connected between the nose adapter and the breathing gas supply.

11. The arrangement according to claim 1, wherein the valve arrangement is configured to be at least partly inflated during inhalation of the patient.

12. The arrangement according to claim 1, wherein the valve arrangement is configured to be at least partly deflated during exhalation of the patient.

13. The arrangement according to claim 1, further comprising:
a bracket arranged to enclose the valve arrangement in a longitudinal extension.

14. The arrangement according to claim 1, wherein the inspiratory air conduit and the nose adapter are constructed as one-piece.

15. The arrangement according to claim 1, wherein the nasal patient interface arrangement is a high flow nasal cannula arrangement ("HFNC arrangement").

16. A breathing apparatus, comprising:
a nasal patient interface arrangement according to claim 1.

17. A method for operating a breathing apparatus, comprising the steps of:
inflating a valve which is substantially enclosed in a first bidirectional gas passage so that the first bidirectional gas passage is at least partly blocked;
providing breathing gas through a second bidirectional gas passage from a pressure gas supply to a nose adapter of a patient so that the patient can inhale the breathing gas, wherein the breathing gas automatically inflates the valve so that the first bidirectional gas passage is blocked only when breathing gas is provided through the second bidirectional gas passage, and wherein the breathing gas is provided automatically at least during a substantial fraction of an inhalation period of the patient; and
deflating the valve so that a gas passage through the first bidirectional gas passage is allowed and so that the majority of exhaled gas from the patient can pass through the first gas passage to ambient air during an exhalation period.

* * * * *